(12) United States Patent
Raa et al.

(10) Patent No.: US 9,820,958 B2
(45) Date of Patent: Nov. 21, 2017

(54) BIOLOGICAL OIL COMPOSITION, FORMULATIONS COMPRISING THE OIL COMPOSITION, AND USE THEREOF TO PREVENT OR TREAT CARDIOVASCULAR DISEASE

(71) Applicant: Calanus AS, Tromso (NO)

(72) Inventors: Jan Raa, Oslo (NO); Gunnar Rorstad, Tromso (NO); Kurt Steinar Tande, Kvaloysletta (NO)

(73) Assignee: Calanus AS, Tromso (NO)

( * ) Notice: Subject to any disclaimer, the term of this patent is extended or adjusted under 35 U.S.C. 154(b) by 125 days.

(21) Appl. No.: 14/305,011

(22) Filed: Jun. 16, 2014

(65) Prior Publication Data

US 2014/0302128 A1    Oct. 9, 2014

Related U.S. Application Data

(62) Division of application No. 13/130,585, filed as application No. PCT/NO2010/000002 on Jan. 4, 2010, now abandoned.

(30) Foreign Application Priority Data

Jan. 5, 2009    (NO) .................................. 20090033

(51) Int. Cl.
| | | |
|---|---|---|
| *A61K 31/202* | (2006.01) | |
| *A61K 31/122* | (2006.01) | |
| *A61K 31/232* | (2006.01) | |
| *A61K 31/045* | (2006.01) | |
| *A61K 31/201* | (2006.01) | |
| *A61K 35/56* | (2015.01) | |
| *A23D 9/013* | (2006.01) | |
| *A23L 33/115* | (2016.01) | |

(52) U.S. Cl.
CPC ............ *A61K 31/202* (2013.01); *A23D 9/013* (2013.01); *A23L 33/115* (2016.08); *A61K 31/045* (2013.01); *A61K 31/122* (2013.01); *A61K 31/201* (2013.01); *A61K 31/232* (2013.01); *A61K 35/56* (2013.01); *A23V 2002/00* (2013.01)

(58) Field of Classification Search
CPC .. A61K 31/122; A61K 31/202; A61K 31/232; A61K 31/045; A61K 31/201; A61K 35/56; A23V 2002/00; A23V 2200/326; A23V 2200/3262; A23V 2250/1868; A23V 2250/187; A23D 9/013; A23L 1/3006; A23L 33/115
See application file for complete search history.

(56) References Cited

U.S. PATENT DOCUMENTS

| | | |
|---|---|---|
| 2002/0025983 A1 | 2/2002 | Horrobin |
| 2006/0188607 A1* | 8/2006 | Schramm ............... A23D 7/005 426/72 |

FOREIGN PATENT DOCUMENTS

| | | | |
|---|---|---|---|
| JP | 10155459 A * | 6/1998 | |
| RU | 2236441 | 9/2004 | |
| WO | WO 9856883 A1 * | 12/1998 | ............. A61K 31/20 |
| WO | 00/23456 | 4/2000 | |
| WO | WO 02092779 A2 * | 11/2002 | ............. A61K 31/20 |
| WO | 2008/132552 | 11/2008 | |

OTHER PUBLICATIONS

Scott et. al., Marine Ecology Progress Series, 2002, vol. 235, pp. 127-134.*
Setnikar et. al., Arzneim.-Forsch./Drug Research, 2005, Cantor Verlag, vol. 55(6), pp. 312-317.*
Spencer et. al., Journal of the American Oil Chemists' Society, 1977, American Oil Chemists' Society, vol. 54, pp. 187-189.*
English translation of office action dated Sep. 7, 2014 from Russian Patent Office.

* cited by examiner

*Primary Examiner* — Sarah Pihonak
(74) *Attorney, Agent, or Firm* — Christian D. Abel

(57) ABSTRACT

This invention relates to a biological oil composition, preferably obtained from a copepod, most preferably the copepod *Calanus finmarchicus* and the use thereof to prevent or treat formation of atherosclerotic plaques and hence development of coronary heart disease. The composition comprises the same marine n-3 polyunsaturated fatty acids (PUFAs) generally regarded as being responsible for the anti-atherosclerotic effect of marine oils, namely EPA (C20:5n-3 eicosapentaenoic acid) and DHA (C22:6n-3 docosahexaenoic acid). However, quite unexpectedly, it has been found that the oil composition of the present invention has a remarkably higher ability to prevent formation of atherosclerotic plaques than what can be attributed to EPA and DHA alone, and moreover, unlike EPA and DHA alone it has a notable blood cholesterol lowering effect.

16 Claims, 3 Drawing Sheets

BIOLOGICAL OIL COMPOSITION, FORMULATIONS COMPRISING THE OIL COMPOSITION, AND USE THEREOF TO PREVENT OR TREAT CARDIOVASCULAR DISEASE

CROSS REFERENCE TO RELATED APPLICATIONS

This is a divisional application of U.S. application Ser. No. 13/130,585 filed May 23, 2011, which is a US National Stage of International application PCT/NO2010/000002 filed 4 Jan. 2010.

FIELD OF INVENTION

The present invention concerns a biological oil composition, formulations comprising the oil composition, and the use of the oil composition in dietary supplements, functional foods and pharmaceutical products for the prevention or treatment of cardiovascular disease.

BACKGROUND OF INVENTION

In the 1970s, Bang, Dyerberg and Nielsen described the plasma lipid and lipoprotein pattern of Eskimos living on the west coast of Greenland, and compared it with that of the Danish population (H. O. Bang, J. Dyerberg and A. B. Nielsen. Plasma lipid and lipoprotein pattern in Greenlandic West-coast Eskimos. Lancet 1971; 1:1143-45). Later, Dyerberg and his collaborators (J. Dyerberg, H. O. Bang and N. Hjørne. Fatty acid composition of the plasma lipids in Greenland Eskimos. American Journal of Clinical Nutrition 1975; 28:958-66) related the differences they found, to the remarkably low mortality from coronary heart disease among the Eskimos, compared to Danes. Since the dietary fat intake was almost the same in the two populations, they suggested that the striking difference in coronary heart disease could be due to the big difference in the intake of marine fats and that coronary heart disease could be associated with the chemical nature of the dietary lipids (J. Dyerberg, H. O. Bang. E. Storffersen, S. Moncada and J. R. Vane. Eicosapentaenoic acid and prevention of thrombosis and atherosclerosis? Lancet 1978; 2:117-19). After these pioneering studies, it became evident that coronary heart disease, which is still among the most serious killer diseases in Western societies, could no longer be regarded merely as a lipid storage disease caused by excessive dietary fat intake.

The scientists who pioneered this research were the first to suggest that the anti-atherogenic factors in the traditional Eskimo diet were marine long chain poly unsaturated fatty acids (PUFAs). Their diet, consisting largely of seal, whale and seabirds, and, to some extent, fish, provided several grams—may be as much as 15 grams—of such fatty acids each day. This is far more than a typical "modern" Western diet contains.

Research during the last 30-40 years has confirmed the classical studies by the Dyerberg group and established a firm scientific foundation for a common understanding among scientists and other professionals: The health benefits of sea-food and marine oils can first and foremost be associated with two typical marine PUFAs, namely eicosapentaenoic acid (EPA) and docosahexaenoic acid (DHA). This statement is in line with the conclusions and recommendations from the symposium "Beyond Cholesterol: Prevention and Treatment of Coronary Heart Disease with n-3 Fatty Acids, published by Deckelbaum et al. (American Journal of Clinical Nutrition 2008; 87(suppl): 2010S-2S).

EPA and DHA contain, respectively, 20 and 22 carbon atoms with 5 and 6 conjugated double bonds, of which the first one is in the position 3 carbon atoms (n-3) counted from the hydrophobic (methyl) end of both these fatty acids. The abbreviation C20:5n-3 is often used as a chemical designation for EPA and C22:6n-3 for DHA. Phytoplankton in the marine environment is the primary producers of EPA and DHA, which follow the food-web from this first trophic level via zooplankton to fish and sea-mammals. Plant food oils and animal fat contain low levels, if any, of EPA and DHA.

EPA and DHA are believed to be particularly important in prevention of cardiovascular disease. Even modest sea-food intake, supplying 250 mg of EPA and DHA daily, seems sufficient to reduce the risk of coronary death by 36% and to reduce mortality in the general population by 17% (U. J. Jung et al. American Journal of Clinical Nutrition 2008; 87(suppl): 2003S-9S).

Physiological and molecular mechanisms proposed to explain the cardioprotective effects of EPA and DHA, include 1) lowering the levels of triacylglycerol and free fatty acids in plasma, 2) increasing high density lipoprotein (HDL) levels and decreasing low density lipoproteins (LDL) levels, 3) decreasing platelet aggregation, 4) decreasing cholesterol delivery and cholesterol deposition in arterial walls, 5) decreasing arterial inflammation. These are interactive mechanisms involving complex and diverse biochemical mechanisms, including effects of EPA and DHA as well as of their transformation products (prostaglandins, prostacycline, thromboxans, leukotrienes) on modulation of immunity and inflammation and gene expression in different cells and tissues. Although the health benefits of EPA and DHA no longer can be questioned, the mechanisms involved are too complex to be fully understood. For instance, it is still a puzzling fact that "the major mechanisms underlying the beneficial effects of n-3 fatty acids in the prevention and treatment of coronary artery disease appears to be distinct from effects on lowering plasma triacylglycerol concentrations" (Deckelbaum et al., American Journal of Clinical Nutrition 2008; 87(suppl): 2010S-2S).

Preclinical and human clinical studies during the last 30-40 years have provided consistent evidence that consumption of sea-food and marine food oils is beneficial for the health, and it has become generally accepted among those skilled in the art that these health benefits are, first and foremost, associated with EPA (eicosapentaenoic acid) and DHA (docosahexaenoic acid). The total evidence related to the ability of these two marine n-3 PUFAs to prevent coronary heart disease is so overwhelming that it has become part of a primary prevention strategy of health authorities in Western societies to recommend daily EPA and DHA consumption. In support of this strategy, it can be referred to the symposium "Beyond Cholesterol: Prevention and Treatment of Coronary Heart Disease with n-3 Fatty Acids" summarized and discussed by R. J. Deckelbaum et al. (American Journal of Clinical Nutrition, 2008; 87 (suppl): 2010S-2S). Moreover, concentrates of EPA and DHA, produced as disclosed in U.S. Pat. Nos. 5,502,077, 5,656,667 and 5,698,594, have been approved by the US Food and Drug Administration (FDA) as pharmaceutical preparations that reduce the level of blood components regarded as risk factors for coronary heart disease.

DETAILED DESCRIPTION OF THE INVENTION

Figure 1:
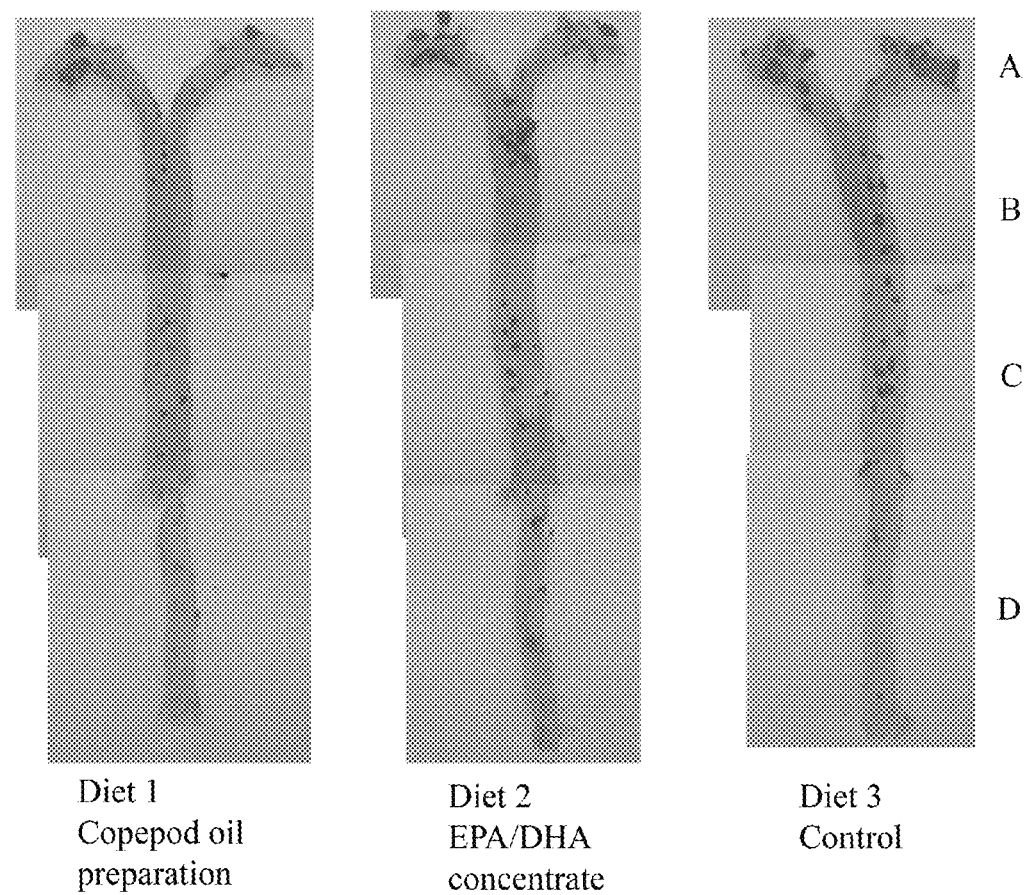
FIG. 1 is a representative visual illustration of plaque formation in aortas of female mice fed a diet to which was added the biological oil composition (Diet 1) or the EPA/DHA-concentrate (Diet 2), compared to the reference diet (Diet 3).

In the description of the present invention below the terms biological oil composition, copepod oil, copepod oil composition, oil composition are used interchangeable.

EPA and DHA are predominant fatty acids present in marine fish, whale, seal and crustaceans. Also, the oil present in the marine copepod *Calanus finmarchicus* is a rich source of EPA and DHA, but this oil differs from other marine oils in a number of other chemical characteristics. Compared to other marine oils, the copepod oil of the present invention is very rich in the C18:4n-3 PUFA (stearidonic acid, SDA). Unlike other common marine food oils, the PUFAs present in the copepod oil exist predominantly as monoesters with long chain monounsaturated alcohols i.e. wax esters. Compared to other common dietary marine oils, the copepod oil of the present invention contains a relatively high proportion of free fatty acids, low amounts of triglycerides, and high levels of astaxanthin and cholesterol.

Based on the common understanding that EPA and DHA are the key factors responsible for the beneficial effects of marine oils in prevention and treatment of coronary artery disease, the biomedical effects of these two fatty acids have been compared with those of the copepod oil composition, as described in the present invention. The effects of the copepod oil according to the present invention have been compared with that of a concentrated EPA/DHA-preparation on atherosclerotic plaque formation and on total cholesterol level in mice, adjusted so that copepod oil provided the same total amount of EPA and DHA as the total amount of EPA and DHA in the reference preparation. In these studies, experimental animals (Apolipoprotein E (ApoE) deficient mice) feeding on an atherogenic high fat (21% w/w) diet containing 0.2% (w/w) cholesterol were used.

Although there are differences in chemical composition between the copepod oil composition of the present invention and other dietary marine oils, the remarkable difference in biological activities, as described in the present invention, could not at all be predicted by anyone working on the effects of marine PUFAs on coronary heart disease. Most striking is the highly unexpected finding that the biological oil composition of the present invention, as opposed to concentrated EPA/DHA, has a statistically significant ability to inhibit formation of atherosclerotic plaques. It also differs from EPA and DHA in the way it affects the pattern of lipid deposition in the body of the experimental animals. The copepod oil described in the present invention is in itself a novel anti-atherosclerotic composition.

The biological oil composition according to the present invention also shows a significant effect on blood cholesterol level. Total blood cholesterol levels are significantly lower in animals fed with a diet comprising the biological oil composition according to the present invention as compared with the levels in animals fed a diet comprising concentrated EPA/DHA The biological oil composition according to the present invention is derived from a marine copepod, preferably a copepod of the genus *Calanus*, such as *Calanus finmarchicus*, using freshly harvested, frozen/thawed or dehydrated raw material. Oil compositions according to the invention may be obtained by any method known to the person skilled in the art such as, but not limited to, conventional fish oil production technology, biotechnological methods, organic solvents or supercritical fluid extraction, or cold pressing. Independent of the procedure of obtaining the oil and the yield of oil, the typical gross composition will be as shown in Table 1. To illustrate the uniqueness of the biological oil composition according to the present invention, the corresponding compositions of conventional fish oil (cod liver oil) and krill oil are shown for comparison. It is evident from this gross chemical analysis that these oils are highly different, in particular regarding their contents of triglycerides, phospholipids, monoesters (wax esters), and of astaxanthin. It should be noted that wax esters constitute the major lipid component in the copepod oil of the present invention, unlike both cod liver oil and krill oil.

TABLE 1

Typical chemical composition of three different marine oils: (A) Copepod oil from *Calanus finmarchicus* caught in Norwegian waters, (B) cod liver oil from Atlantic cod *Gadus morhua*, and (C) krill oil from *Euphausia superba* caught in the Southern ocean, given in mg/g oil.

| Lipid classes | A[1] | B[2] | C[3] |
|---|---|---|---|
| Triglycerides | 60 | 955 | 260 |
| Free fatty acids | 80 | 14 | 13 |
| Fatty alcohols | 62 | 0 | 0 |
| Saturated fatty acids | 190 | 160 | 300 |
| Monounsaturated | 125 | 385 | 300 |
| Polyunsaturated | 270 | 475 | 387 |
| n-3 fatty acids | >250 | 395 | 332 |
| n-6 fatty acids | <15 | 50 | 55 |
| Cholesterol | 40 | 12 | 50 |
| Wax esters (fatty acid/alcohol esters) | 650 | 0 | 0 |
| Polar lipids (phospholipids, free fatty acids, free fatty alcohols) | 200-260 | 18 | 670 |
| Neutral lipids (triglycerides, wax esters, cholesterol) | 740-800 | 967 | 310 |

[1]Copepod oil produced by Calanus AS (www.calanus.no).
[2]From Falch, E., Rustad, T., and Aursand, M. By-products from gadiform species as raw material for production of marine lipids as ingredients in food or feed. *Process Biochemistry* 2006; 41: 666-674.
[3]From Phleger, C. F., Nelson, M. N., Mooney, B. D., and Nichols, P. D. Interannual and between species comparison of the lipids, fatty acids, and sterols of Antarctic krill from the US AMLR Elephant Island survey area. *Comparative Biochemistry and Physiology* Part B 2002; 131: 733-747.

Besides the notable difference in gross chemical composition (Table 1), the three marine oils used here for illustration purposes, are highly different also in their content of individual fatty acids (Table 2).

TABLE 2

Fatty acid composition of three different marine oils: (A) Copepod oil from *Calanus finmarchicus* caught in Norwegian waters, (B) cod liver oil from Atlantic cod *Gadus morhua*, and (C) krill oil from *Euphausia superba* caught in the Weddell Sea, given in mg/g oil.

| Fatty acids | A[1] | B[2] | C[3] |
|---|---|---|---|
| 14:0 FA (myristic) | 108 | 40 | 119 |
| 15:0 FA | 6 | 0 | 0 |

TABLE 2-continued

Fatty acid composition of three different marine oils: (A) Copepod oil from *Calanus finmarchicus* caught in Norwegian waters, (B) cod liver oil from Atlantic cod *Gadus morhua*, and (C) krill oil from *Euphausia superba* caught in the Weddell Sea, given in mg/g oil.

| Fatty acids | A[1] | B[2] | C[3] |
|---|---|---|---|
| 16:0 FA (palmitic) | 72 | 112 | 209 |
| 16:1 n-9 | 1.8 | 0 | 0 |
| 16:1 n-7 FA | 16 | 61 | 0 |
| 16:1 n-5 FA | 0 | 0 | 56 |
| 17:0 FA | 1.7 | 0 | 0 |
| 16:2 n-4 FA | 1.7 | 0 | 0 |
| 18:0 FA | 4.5 | 27 | 15 |
| 16:3 n-3 | 0.8 | 0 | 0 |
| 18:1 n-9 FA (oleic) | 23.4 | 167 | 170 |
| 16:4 n-3 | 2.2 | 0 | 0 |
| 18:1 n-7 FA | 2.8 | 40 | 70 |
| 18:2 n-6 FA | 10.2 | 19 | 25 |
| 18:3 n-3 FA | 24.4 | 14 | 9 |
| 20:0 FA | 0 | 0 | 0 |
| 18:4 n-3 FA (stearidonic, SDA) | 109.7 | 21 | 51 |
| 20:1 n-11 FA | 5.3 | 0 | 0 |
| 20:1 n-9 FA (gadoleic) | 27 | 98 | 13 |
| 20:4 n-6 FA | 2.0 | 8 | 7 |
| 20:4 n-3 FA | 9.0 | 0 | 0 |
| 22:1 n-11 (+20:4 n-3 FA) | 42.7 | 8.5 | 0 |
| 22:1 n-9 FA | 2.7 | 0 | 0 |
| 20:5 n-3 FA (eicosapentaenoic, EPA) | 67.0 | 72 | 128 |
| 22:4 n-6 FA | 10.5 | 0 | 0 |
| 24:1 n-9 FA | 2.9 | 0 | 0 |
| 22:5 n-3 FA | 3.7 | 20 | 0 |
| 22:6 n-3 FA (docosahaexaenoic, DHA) | 54.7 | 188 | 101 |
| Sum identified | 612.7 | 895.5 | 973 |

[1]Copepod oil produced by Calanus AS (www.calanus.no).
[2]From Standal, I. B., Praël, A., McEvoy, L., Axelson, D. E., and Aursand, M. Discrimination of Cod Liver Oil According to Wild/Farmed and Geographical Origins by GC and 13C NMR. *J. Am Oil Chem Soc* 2008; 85: 105-112.
[3]From Hagen, W., Kattner, G., Terbrüggen, A., and Van Vleet, E. S. Lipid metabolism of the Antarctic krill *Euphausia superba* and its ecological implications. *Marine Biology* 2001; 139: 95-104.

The most noteworthy difference in fatty acid composition between the three oils, is the very high stearidonic acid (SDA) content in the copepod oil.

In the oil composition of the present invention, SDA, EPA and DHA exist to a large extent as esters with long chain alcohols. A typical composition of wax esters and long chain alcohols in the copepod oil of the present invention is shown in Table 3.

TABLE 3

Typical composition of wax esters and alcohol/fatty acid combinations (% (w/w)) in copepod oil derived from *Calanus finmarchicus*.[1]

| Wax ester | Major alcohol/ fatty acid | Minor alcohol/ fatty acid | % (w/w) |
|---|---|---|---|
| 30:1 | 14:0/16:1 | 16:1/14:0 | 0.8 |
| 32:1 | 16:0/16:1 | 14:0/18:1 | 1.9 |
| 32:2 | 16:1/16:1 | 14:0/18:2 | 0.6 |
| 32:4 | 14:0/18:4 | 16:0/16:4 | 0.9 |
| 34:1 | 16:0/18:1 | 14:0/20:1 | — |
|  | 20:1/14:0 |  | 17.6 |
| 34:2 | 16:0/18:2 | 16:1/18:1 | 0.9 |
| 34:3 | 16:0/18:3 | 16:1/18:2 | — |
| 34:4 | 16:0/18:4 | 16:1/18:3 | 2.7 |
| 34:5 | 14:0/20:5 | 16:1/18:4 | 0.4 |
| 36:1 | 20:1/16:0 | 16:0/20:1 | — |
|  | 22:1/14:0 |  | 21.9 |
| 36:2 | 20:1/16:1 | 16:1/20:1 | 2.3 |
| 36:5 | 16:0/20:5 | 20:1/16:4 | 1.1 |
| 36:6 | 16:1/20:5 | 14:/22:6 | 0.3 |
| 38:1 | 22:1/16:0 | 16:0/22:1 | 2.8 |
| 38:2 | 22:1/16:1 | 20:1/18:1 | 3.9 |
| 38:3 | 20:1/18:2 | 22:1/16:2 | 0.4 |

TABLE 3-continued

Typical composition of wax esters and alcohol/fatty acid combinations (% (w/w)) in copepod oil derived from *Calanus finmarchicus*.[1]

| Wax ester | Major alcohol/ fatty acid | Minor alcohol/ fatty acid | % (w/w) |
|---|---|---|---|
| 38:4 | 20:1/18:3 | 22:1/16:3 | 0.9 |
| 38:5 | 20:1/18:4 | 22:1/16:4 | 5.4 |
| 38:6 | 16:0/22:6 | 16:1/22:5 | — |
| 40:2 | 20:1/20:1 | 22:1/18:1 | 5.9 |
| 40:3 | 22:1/18:2 |  | 0.7 |
| 40:5 | 22:1/18:4 | 20:1/20:4 | 4.7 |
| 40:6 | 20:1/20:5 |  | 1.5 |
| 42:2 | 22:1/20:1 | 20:1/22:1 | 12.7 |
| 42:6 | 22:1/20:5 | 20:1/22:5 | 1.5 |
| 42:7 | 20:1/22:6 |  | 2.0 |
| 44:2 | 22:1/22:1 |  | 4.9 |
| 44:7 | 22:1/22:6 |  | 0.6 |

[1] Compiled from Graeve, M. and Kattner, G. Species-specific differences in intact wax esters of *Calanus hyperboreus* and *C. finmarchicus* from Fram Strait - Greenland Sea. *Marine Chemistry* 1992; 39: 269-281.

In conclusion, the copepod oil of the present invention differs markedly from typical fish oil and krill oil in both gross chemical composition and fatty acid content. However, like other marine oils it comprises EPA and DHA.

In spite of its high wax-ester content, the oil composition of the present invention is a low-viscous and completely free-flowing liquid at room-temperature. One of the reasons for this is that the alcohols of the wax esters are predominated by medium-length monounsaturated alcohols, typically 80% or more (mainly C20:1 and C22:1).

Depending on the analytical methods used, the typical content of wax-ester of the oil composition of the present invention is 70-90%, whereas it contains 10-20% of other components such as free fatty acids, triacylglycerols, sterols and pigments. In certain applications, it may be advantageous or even desirable to remove free fatty acids and other components by suitable methods known to those skilled in the art. Thus, in one embodiment of the preset invention the oil composition may contain up to 100% wax ester.

It has been found that the copepod oil according to the present invention has markedly different biological effects than a concentrated preparation of EPA and DHA used in the same concentration as in the copepod oil. Particularly the composition according to the present invention prevents the formation of atherosclerotic plaque and thus is useful in the prevention and treatment of cardiovascular disease. The composition according to the present invention is also found to have an effect on the total blood cholesterol level and is useful in the prevention and treatment of hypercholesterolaemia and elevated blood cholesterol levels.

The biological oil composition according to the present invention comprises from 20%, 25%, 30%, 35%, 40%, 45%, 50%, 55%, 60%, 65%, 70%, by weight up to 75%, 80%, 85%, 86%, 87%, 88%, 89% 90%, 91%, 92%, 93%, 94%, 95%, 96%, 97%, 98%, 99%, 100% by weight of wax esters. Preferably the biological oil composition comprises from 80%, 81%, 82%, 83%, 84%, 85%, 86%, 87% 88%, 89% by weight up to 90%, 91%, 92%, 93%, 94%, 95%, 96%, 97%, 98%, 99%, 99.5%, 100% by weight of wax esters.

Further the biological oil composition of the present invention comprises from 5%, 6%, 7%, 8%, 9%, 10% by weight up to 11%, 12%, 13%, 14%, 15%, 16%, 17%, 18%, 19%, 20% by weight of SDA.

The content of EPA in the biological oil composition may be 3%, 4%, 5%, 6%, 7%, by weight up to 8%, 9%, 10%, 11%, 12%, 13%, 14%, 15% by weight. The composition may comprise 2%, 3%, 4%, 5% by weight up to 6%, 7%, 8%, 9%, 10% by weight of DHA.

In one embodiment, the present invention provides a biological oil composition wherein the composition comprises 20-100% by weight of wax esters, preferably 50-100% by weight of wax esters, more preferred 70-100% by weight of wax esters for use as a medicament for the prevention and treatment of cardiovascular disease. The oil composition may be isolated from a marine copepod, preferably one of the genus *Calanus*, and more preferably said copepod is of the species *Calanus finmarchicus*.

In other embodiments of the invention the present invention provides a biological oil composition for the use as a medicament in the prevention and treatment of atherosclerosis, hypercholesterolaemia and elevated blood cholesterol levels.

In another embodiment the present invention provides an oil composition that further comprises 5-20% by weight of SDA.

In yet another embodiment the present invention provides an oil composition comprising 3-15% by weight of EPA and 2-10% by weight of DHA.

In a further embodiment of the present invention an oil composition comprising 20-100% by weight of wax esters, preferably 70-100% by weight of wax esters, 5-20% by weight of SDA, 3-15% by weight of EPA and 2-10% by weight of DHA is provided.

In another embodiment of the present invention an oil composition comprising fatty alcohols and SDA, DHA and EPA as monoester with fatty alcohols is provided.

In a further embodiment the present invention provides an oil composition comprising 1000-4000 ppm of astaxanthin, mainly in esterified form.

A dietary supplement formulation comprising an oil composition as described above is also provided by the present invention.

A functional food formulation comprising an oil composition as described above is also encompassed by the present invention.

In yet another embodiment of the present invention a pharmaceutical formulation comprising an oil composition as described above is provided.

The formulation according to the invention comprising an oil composition as described above may be provided in capsules, tablets, emulsions or tonics and may comprise one or more pharmaceutically acceptable additive selected from the group consisting of adjuvans, antioxidants, emulsifiers, surfactants and carriers.

The present invention further provides the use of an oil composition as described above for the manufacturing of a product for the prevention or treatment of a cardiovascular disease, particularly atherosclerosis, hypercholesterolaemia and elevated blood cholesterol levels.

The present invention also provides a method for the prophylaxis or treatment of cardiovascular disease, particularly atherosclerosis, hypercholesterolaemia and elevated blood cholesterol levels wherein the individual in need of such prophylactic or curative treatment is orally administered with a pharmaceutical composition comprising a biological oil composition wherein the composition comprises 20-100% by weight of wax esters, preferably 50-100% by weight of wax esters, more preferred 70-100% by weight of wax esters, and wherein a daily dosage level in the range of 4-100 mg/kg body weight.

In another embodiment the present invention provides a method wherein the administered pharmaceutical composition further comprises 5-20% by weight of SDA.

In yet another embodiment the present invention provides a method wherein the pharmaceutical composition comprising 3-15% by weight of EPA and 2-10% by weight of DHA.

In a further embodiment of the present invention a method wherein the administered pharmaceutical composition comprises 20-100% by weight of wax esters, preferably 70-100% by weight of wax esters, 5-20% by weight of SDA, 3-15% by weight of EPA and 2-10% by weight of DHA is provided.

In another embodiment of the present invention a method wherein the administered pharmaceutical composition comprising fatty alcohols and SDA, DHA and EPA as monoester with fatty alcohols is provided.

In a further embodiment the present invention provides a method wherein the administered pharmaceutical composition comprises 1000-4000 ppm of astaxanthin, mainly in esterified form. The following non-limiting experimental part and examples illustrate and document the present invention.

EXAMPLES

Experimental

When studying the preventive efficacy of any drug candidate or dietary ingredient on coronary heart disease, the most reliable end-point analyses are the actual disease manifestations, such as, for instance, formation of atherosclerotic plaques. Effects on blood parameters considered to be indicative of the risk of disease development are of course important for evaluation of mode of action of new anti-atherogenic drug candidates, but it is preferable to relate such blood analyses to efficacy data on the disease manifestation itself. This has been the philosophy in the studies constituting the foundation of the present invention.

The biological effects of the copepod oil of this invention were recorded in mice deficient in apolipoprotein E (ApoE). Mice of this strain are routinely used to determine effects of dietary components on development of vascular inflammation and atherosclerotic plaques, since they develop atherosclerotic lesions according to a pattern very similar to that of humans, and they are useful model animals for studies of biochemical and cellular processes involved in initiation, progression and regression of atherotrombotic disease. The studies were carried out at the Faculty of Medicine at the University of Tromsø (Norway). Three groups of ten female mice were installed at an age of 7 weeks and fed 3 different diet treatments (see below) for 13 weeks.

The mice were fed ad libitum with an experimental high fat (21% w/w) and cholesterol (0.2% w/w) diet, rich in bioavailable carbohydrates (sugar/dextrin) and with a high proportion of saturated fat (sniff Spezialdiaten GmbH, sniff EF Clinton/Cybulsky (II) mod.). The composition of this diet promotes development of obesity and of atherosclerotic lesions. The diet was added either 1% (w/w) of the copepod oil of the present invention (Diet 1) or 0.1223% (w/w) of an EPA/DHA-concentrate (Diet 2), producing two experimental feeds with equal contents of EPA and DHA. The cholesterol content of these two diets and of the control diet (Diet 3) without added oil was adjusted to 0.20% by adding cholesterol, taking into account the cholesterol present in the feed ingredients and in the copepod-oil itself. The composition of the experimental diets is shown in Table 4.

TABLE 4

Experimental diet for rats and mice with high fat/cholesterol content (type ssniff® EF Clinton/Cybulsky (II) mod.)[1] with ingredient and nutritional profile for the three test groups

|  | Diet 1 Copepod oil preparation | Diet 2 EPA/DHA concentrate | Diet 3 Control |
|---|---|---|---|
| Ingredients |  |  |  |
| Sucrose, % | 33.0876 | 33.0476 | 32.5867 |
| Milk fat, % | 19.9692 | 19.9692 | 19.9692 |
| Casein (vitamin free), % | 19.4700 | 19.4700 | 19.4700 |
| Maltodextrin, % | 9.9846 | 9.9846 | 9.9846 |
| Corn starch, % | 4.9923 | 4.9923 | 4.9923 |
| Powdered cellulose, % | 4.9923 | 4.9923 | 4.9923 |
| AIN-76 Mineral Mix, % | 3.4946 | 3.4946 | 3.4946 |
| Calanus Oil-841, % | 1.0000 | — | — |
| Omacor Oil-842, % | — | 0.1223 | — |
| AIN-76A Vitamin Mix, % | 0.9985 | 0.9985 | 0.9985 |
| Corn Oil, % | 0.9985 | 0.9985 | 1.9985 |
| Calcium carbonate, % | 0.3994 | 0.3994 | 0.3994 |
| DL-Methionine, % | 0.2995 | 0.2995 | 0.2995 |
| Choline bitartrate, % | 0.1997 | 0.1997 | 0.1997 |
| Cholesterol, % | 0.1498 | 0.1498 | 0.1498 |
| Ethoxyquin, % | 0.0040 | 0.0040 | 0.0040 |
| Nutritional profile |  |  |  |
| Protein, % | 17.4 | 17.4 | 17.4 |
| Fat, % | 21.0 | 21.0 | 21.0 |
| Cholesterol, ppm | 2 027 | 2 027 | 2 027 |
| Carbohydrates, % | 48.9 | 48.9 | 48.4 |
| Fiber (max), % | 5.0 | 5.0 | 5.0 |
| Energy, kcal/g | 4.48 | 4.56 | 4.55 |
| From |  |  |  |
| Protein, % | 15.3 | 15.3 | 15.4 |
| Fat (ether extract), % | 41.6 | 41.7 | 41.8 |
| Carbohydrates, % | 43.0 | 43.0 | 42.8 |

[1] Produced by ssniff Spezialdiäten GmbH (www.ssniff.de).

The copepod oil preparation was an experimental product provided by Calanus AS, Tromsø, Norway (www.calanus.no). The EPA/DHA concentrate used as reference test substance was the lipid lowering drug Omacor (Pronova Biopharma ASA, P.O. Box 420, NO-1327 Lysaker, Norway). According to the manufacturer (www.pronova.com) this product contains 90% omega-3-acid ethyl esters of EPA (460 mg/g) and DHA (380 mg/g) and is manufactured using fish oil as a starting material.

The experimental mice were monitored daily, and weighed at regular intervals. Samples of blood serum were taken at different points for later analysis of various blood parameters including lipids and fatty acids. The mice were sacrificed at the end of the experiment, and all relevant organs were dissected out following standard procedures. Following dissection of the sacrificed mice, the aortas were isolated, cleaned and cut open longitudinally, pinned to a white cardboard and fixed in 10% formalin for at least 24 hours. The aortas were stained with Oil Red O (Sigma) before analysis. After rinsing, the aortas were mounted on microscopic slides, and images (2,700 dpi) were acquired using a SprintScan 35 scanner (Polaroid, Cambridge, Mass., USA) equipped with GeoScan Enabler (Meyer Instruments, Houston, Tex., USA). The images were analyzed for positive areas, adopting the state-of-the art calibration and image analyses methodology. The total lesion area was quantified in each group by computer-assisted quantitative morphometry as described by N. V. Guevara et al. (The absence of p53 accelerates atherosclerosis by increasing cell proliferation in vivo. *Nature Medicine* 1999; 5:335-339).

Biological Effects
i) Atherosclerosis

It has been found that the copepod oil of the present invention has markedly different biological effects than a concentrated preparation of EPA and DHA used in the same concentration as in the copepod oil. This was a highly unexpected finding, considering the overwhelming consensus among the skilled in the art, that the positive health effects of marine oils are associated with their content of EPA and DHA, exclusively.

Figure 2:
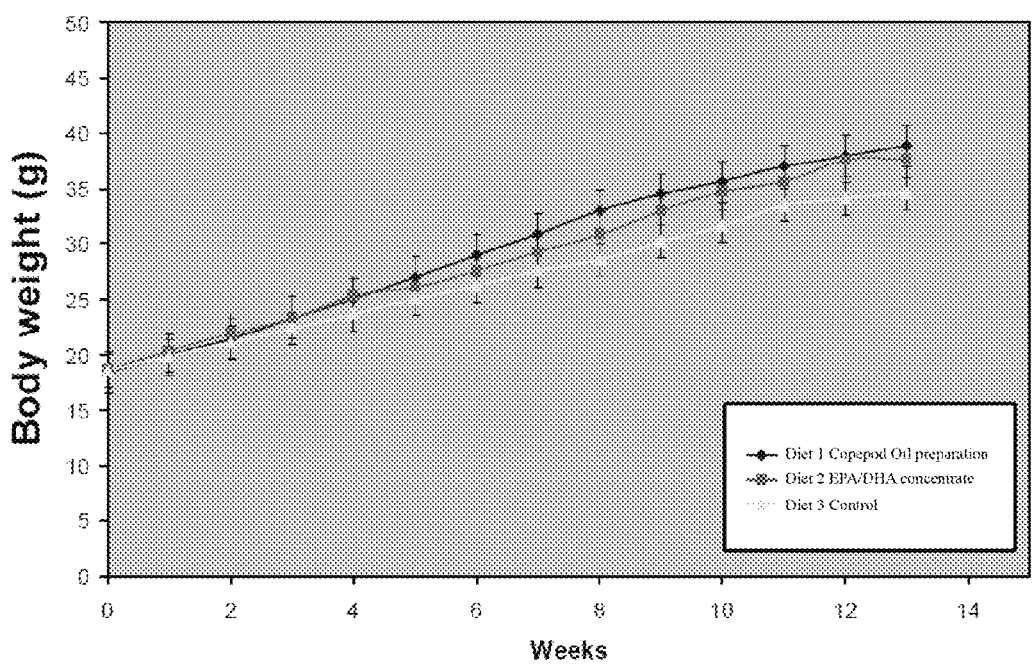
FIG. 2 illustrates the average growth of female mice (n=10) on the three experimental diets.
Figure 3:
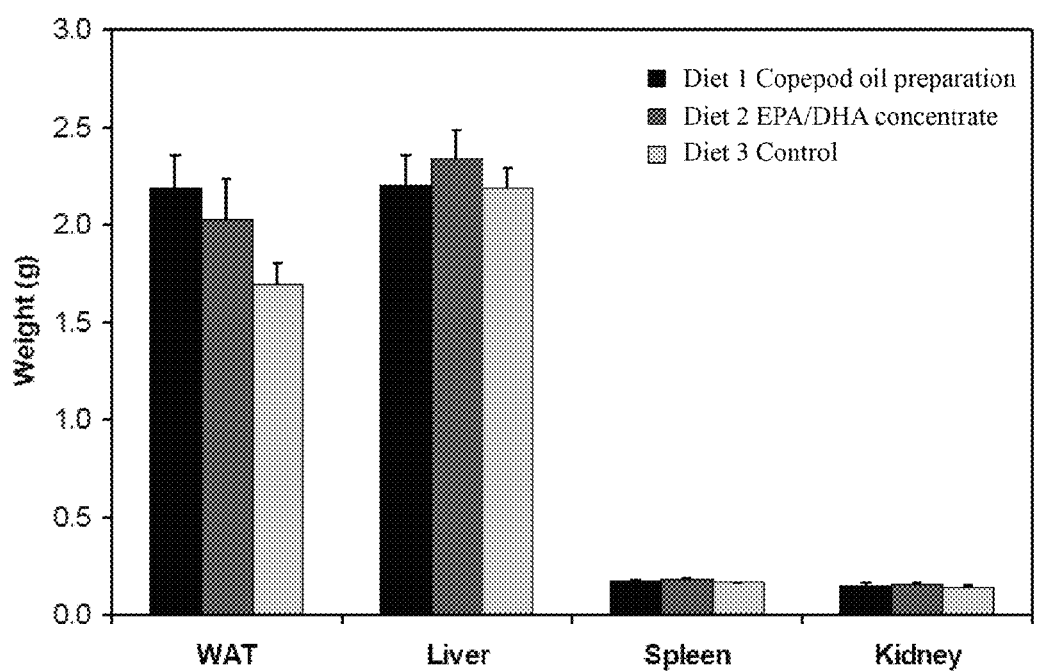
FIG. 3 shows the average weight of different organs of female mice (n=10) fed the three experimental diets (WAT=white adipose tissue).

The results are shown in Table 5 and in FIGS. 1-3.

The effect of the copepod oil of the present invention and of EPA/DHA-concentrate on atherosclerotic plaque formation in the aortas of female mice is shown in Table 5. The copepod oil preparation had a striking and statistically highly significant effect on reduction of plaque formation both in the aortic arch (p=0.002) and the total aorta (p=0.001) compared to control. Also the EPA/DHA-concentrate reduced plaque formation compared to control, but the effect did not meet the requirements of statistical significance.

TABLE 5

The effect of a copepod oil preparation and of concentrated EPA/DHA on atherosclerotic plaque formation[1] in the ascending aortic arch, thoracal, abdominal and perirenal segments of the aorta in female mice.

| Target region | Diet 1 Copepod oil preparation (n = 10) | Diet 2 EPA/DHA concentrate (n = 10) | Diet 3 Control (n = 10) |
|---|---|---|---|
| Aortic arch (A) | 15.1 | 18.0 | 22.0 |
| Thoracal (B) | 7.93 | 9.51 | 12.16 |
| Abdominal (C) | 1.93 | 2.52 | 3.94 |
| Perirenal (D) | 1.36 | 2.27 | 1.94 |
| Total aorta (B-D) | 4.59 | 5.87 | 7.22 |

[1]The figures represent the average lesion area in percent of total area of each target region at time of sacrifice. See FIG. 1 for the subdivision of target regions (A-D) of the aorta.

Growth of the mice is shown in FIG. 2. Although the mice grew fastest on feed enriched with copepod oil, and thrived well on that diet, this apparent difference does not meet the requirements for statistical significance. There was no difference between the groups in feed intake and no negative effects could be observed on animals fed the experimental diets.

Weight of different organs is shown in FIG. 3. Although there was a higher level of fat deposited in the white adipose tissue (WAT) in mice fed the copepod oil, the difference was not statistically significant. However, it is a noteworthy observation indeed that the copepod oil of the present invention reduces plaque formation while more lipids are deposited in lipid storage tissues.

ii) Blood Cholesterol Level

The copepod oil has a notably more pronounced antiatherosclerotic effect than purified EPA and DHA at same concentration as in this oil. The mechanisms involved in this effect of the copepod oil may accordingly be additive to the EPA- and DHA-effects or be entirely different.

The results shown in Table 6 illustrate that Calanus Oil differs from EPA and DHA also regarding the effect on blood cholesterol level in the experimental animals. Whereas the cholesterol level in blood of animals fed the EPA/DHA-diet was the same as in control animals after 13 weeks of feeding, the cholesterol level in blood of the Calanus Oil group was notably lower. Both treatment groups seem to have a slight, and similar, triglyceride lowering effect compared to control.

TABLE 6

Effects of the dietary supplements on bodyweight, food intake and plasma lipids in apoE-deficient female mice after 13 weeks of treatment, as mean values +− SEM.

| Female apoE-deficient mice | Diet 1 Copepod oil composition (n = 10) | Diet 2 EPA/DHA concentrate (n = 10) | Diet 3 Control (n = 10) |
|---|---|---|---|
| Bodyweight (g) | | | |
| Initial | 18.4 +/− 0.3 | 18.7 +/− 0.3 | 18.6 +/− 0.4 |
| Final | 38.9 +/− 1.2 | 37.7 +/− 1.6 | 34.6 +/− 1.2 |
| Food intake (g/day) | 2.72 +/− 0.05 | 2.72 +/− 0.07 | 2.77 +/− 0.04 |
| Total cholesterol (mmol/L) | 12.3 +/− 1.25 | 15.9 +/− 1.28 | 16.1 +/− 1.25 |
| Triacylglycerol (mmol/L) | 0.82 +/− 0.05 | 0.84 +/− 0.07 | 0.96 +/− 0.05 |

The invention claimed is:

1. A method for the treatment of, or reducing the risk of contracting, a cardiovascular disease comprising administering to a patient in need thereof a clinically effective dosage of a composition comprising 20-100% by weight of wax esters, wherein said wax esters consist of monoesters of mono—or polyunsaturated C16 to C22 fatty acids and monounsaturated C16 to C22 fatty alcohols, wherein the composition is isolated from a copepod of the genus *Calanus*.

2. The method according to claim 1, wherein the copepod species is *Calanus finmarchicus*.

3. The method according to claim 1 or 2, wherein said cardiovascular disease is atherosclerosis.

4. The method according to claim 1 or 2, wherein said cardiovascular disease is hypercholesterolaemia.

5. The method according to claim 1 or 2, wherein the composition comprises 40-85% by weight of wax esters.

6. The method according to claim 1 or 2, wherein 70% or more of the monounsaturated fatty alcohols of the wax esters are C16:1, C20:1 and C22:1.

7. The method according to claim 1 or 2, wherein 70% or more of the fatty alcohols of the wax esters are monounsaturated, and wherein 50% or more of the fatty acids of the wax ester are either mono- or polyunsaturated n-3 fatty acids.

8. The method according to claim 1 or 2, wherein 5-20% by weight of the composition is wax esters having stearidonic acid (SDA) as their fatty acid component.

9. A method according to claim 8, wherein 3-15% by weight of the composition is wax esters having eicosapentaenoic acid (EPA) as their fatty acid components and wherein 2-10% by weight of the composition is wax esters having docosahexaenoic acid (DHA) as their fatty acid components.

10. A method according to claim 1 or 2, wherein the wax esters of the composition comprise a combination of monoesters of SDA, DHA and EPA as the fatty acid component.

11. The method according to claim 1 or 2, wherein the composition further comprises 100-4000 ppm of astaxanthin.

12. The method according to claim 1 or 2, wherein the clinically effective dosage is a daily amount of 4-100 mg/kg body weight of the oil composition.

13. The method according to claim 1 or 2, wherein the composition is provided as a pharmaceutical composition in capsules, tablets, emulsions or tonics.

14. A method according to claim 13, comprising administering to a patient in need thereof a clinically effective dosage of a composition further comprising one or more pharmaceutically acceptable additives selected from the group consisting of adjuvants, antioxidants, emulsifiers, surfactants and carriers.

15. The method according to claim 1 or 2, wherein the composition comprises 70-100% by weight of wax esters.

16. The method according to claim 1 or 2, wherein the fatty acid component of the wax ester is stearidonic acid (SDA) and the fatty alcohol component of the wax ester is C22:1 n-11.

\* \* \* \* \*